United States Patent [19]

Sabatucci

[11] Patent Number: 5,336,687

[45] Date of Patent: Aug. 9, 1994

[54] INHIBITION OF BONE LOSS BY 4-ARYLOXY-5-HYDROXY-2(5H)-FURA-NONES

[75] Inventor: Joseph P. Sabatucci, Cranbury, N.J.

[73] Assignee: American Home Products Corporation, Madison, N.J.

[21] Appl. No.: 101,885

[22] Filed: Aug. 4, 1993

[51] Int. Cl.$^5$ .................. C07D 307/62; A61K 31/34
[52] U.S. Cl. ...................................... 514/473; 549/315
[58] Field of Search ......................... 549/315; 514/473

[56]         - References Cited
        U.S. PATENT DOCUMENTS

| 3,981,857 | 9/1976 | Habu et al. | 549/315 |
| 4,516,241 | 4/1990 | Haywood | 549/313 |
| 4,839,385 | 6/1989 | Maullem et al. | 514/473 |
| 4,874,782 | 10/1989 | Bonjouklian et al. | 514/473 |
| 5,026,725 | 6/1991 | Hayward et al. | 514/473 |

OTHER PUBLICATIONS

Chem. Abstr. 79(9): 53245w (Krawcynska et al., 1973).
Kharode, et al, J. Bone Min. Res. 2 (Suppl.), 358 (1987).

Primary Examiner—Johann Richter
Assistant Examiner—John D. Peabody
Attorney, Agent, or Firm—R. F. Boswell, Jr.

[57]         ABSTRACT

This invention relates to 4-phenoxy (and 4-substituted phenoxy)5-hydroxy-2(5H)-furanones of the formula:

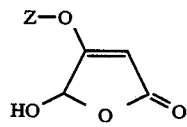

where Z is

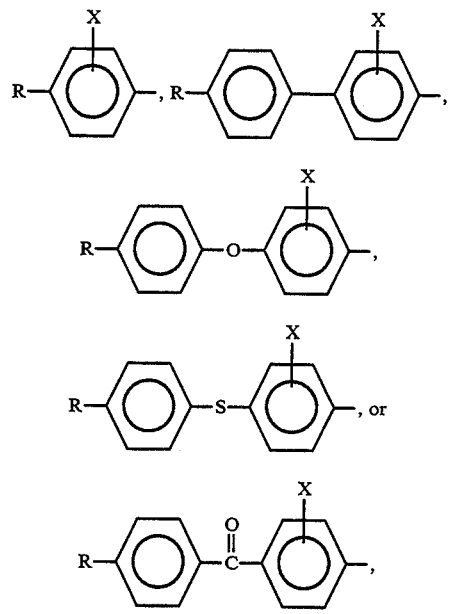

where R is H, halogen, $C_1$-$C_8$ alkyl, $C_3$-$C_8$ cycloalkyl, trifluoromethyl, or

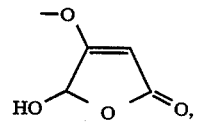

and X is H, $C_1$-$C_8$ alkyl, —O—$C_1$-$C_8$ alkyl, or halogen; a process for their preparation, their use in the treatment of osteoporosis, and pharmaceutical compositions thereof.

11 Claims, No Drawings

INHIBITION OF BONE LOSS BY 4-ARYLOXY-5-HYDROXY-2(5H)-FURANONES

This invention relates to 4-aryloxy-5-hydroxy-2(5H)-furanones, to the process for their preparation, to pharmaceutical compositions containing the 4-aryloxy-5-hydroxy-2(5H)-furanones and to their use for modifying the balance between bone resorption and bone production in a mammal to effect a decrease in bone mass loss due to osteoporosis.

BACKGROUND OF THE INVENTION

Bone tissue constantly undergoes the coupled processes of bone formation by osteoblasts and bone resorption by osteoclasts termed remodeling. Bone mass is increased when bone formation exceeds bone resorption. Osteoporosis is a common skeletal disorder affecting nearly 20 million Americans mostly over the age of 45 adversely effecting the dynamic bone remodeling process and resulting in 1.2 million fractures annually [S. L. Bonnick, J. Am. Med. Women's Assoc., 45 75 (1990)]. It is thought to be caused by an imbalance between bone resorption and bone formation such that there is a net loss of bone and reduction in bone mineral density. Several kinds of osteoporosis are recognized: senile (due to aging), postmenopausal (due to estrogen-depletion following menopause), disuse (due to immobilization) and steroid-induced. Current treatments focus on preventing the bone loss with calcitonin, estrogen or bisphosphonates, ensuring an adequate supply of calcium to the bone with vitamin D and calcium or attempting to stimulate bone formation with fluoride. As formation of bone is "coupled" to previous resorption of bone, preventing bone loss can itself result in a small increase in bone mass (approx. 5%) due to the filling of resorption cavities by osteoblasts in the absence of any loss of bone elsewhere in the skeleton, a point which needs to be borne in mind when interpreting clinical data.

Estrogen replacement therapy has been the treatment of choice in women. To be effective in preventing osteoporosis it may need to be taken for 5 to 10 years [Christiansen, C. and Lindsay R. "Estrogens, bone loss and preservation." *Osteoporosis International* 1990; 1:15–21] and this presents compliance problems and is further associated with increased risk of certain types of cancers. Treatment with sodium fluoride which is mitogenic for osteoblasts may result in bone density increase up to 8–10% a year. However, significant side-effects have also been reported, and the bone growth is irregular and fracture incidence does not appear to be significantly lowered. The class of drugs currently under development are the bisphosphonates. Treatment with these organic phosphates produces a sustained increase in bone mass for several years, but some side effects that occur are renal failure, hypotension and extra-skeletal calcification. Thus none of the present treatments are entirely suitable for the treatment of osteoporosis.

PRIOR ART

U.S. Pat. No. 4,916,241 discloses 4-arylmethylene-5-hydroxy-2(5H)furanones of the formula:

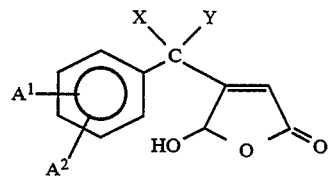

where X is —H or —OH and Y is —H or —$C_1$–$C_6$ alkyl and $A^1$ and $A^2$ are independently phenyl, loweralkoxy, aryloxy or halogen or $A^1$ and $A^2$ together are —O—$CH_2$—O—. Compounds of the present invention differ in that the aromatic group is linked to the 5-hydroxy-2(5H)furanone-4-yl group through an oxygen link and that two 5-hydroxy-2(5H)furanone-4-yl groups may be present.

Certain 3-substituted-4-phenoxy (and 4-phenylthio)-5-hydroxy-5H-furan-2-ones having fungicidal properties have been disclosed in Przem. Chem. 52(4), 276–9 (1973) and Zh. Obshch. Khim. 44(2), 390–2 (1974).

SUMMARY OF THE INVENTION

The novel compounds of this invention are represented by the formula:

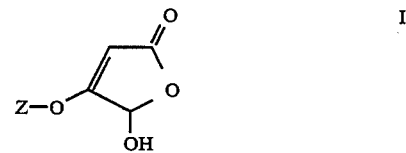

where Z is a moiety selected from:

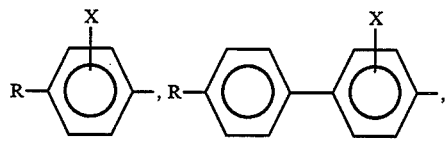

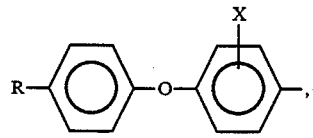

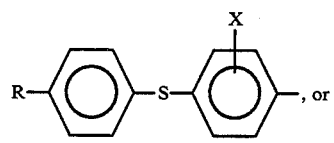

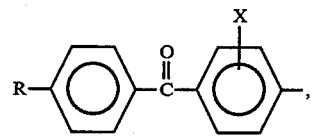

where R is H, $C_1$–$C_8$ alkyl, $C_3$–$C_8$ cycloalkyl, halogen, trifluoromethyl, or 5-hydroxy-2(5H)furanone-4-yloxy, and X is H, $C_1$–$C_8$ alkyl, —O—$C_1$–$C_8$ alkyl or halogen.

The most preferred compounds of this invention are those where Z is

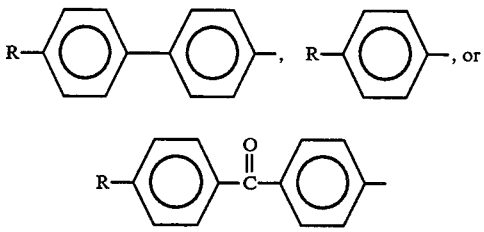

and R is fluoro, cyclopentyl, or 5-hydroxy-2(5H)furanone-4-yloxy.

In the above definitions, halogen is fluorine, chlorine, bromine or iodine. The term $C_1$–$C_8$ alkyl includes straight and branched chain hydrocarbon groups.

DETAILED DESCRIPTION OF THE INVENTION

The compounds of this invention are prepared according to the novel process outlined in Scheme I.

Scheme I

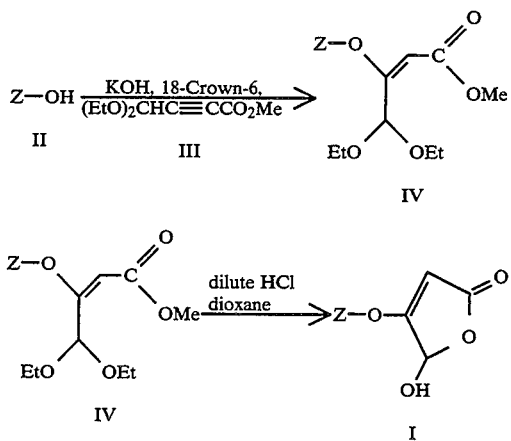

In this reaction scheme, a phenol II is reacted with a 4,4-dialkoxy-2-butynoic acid alkyl ester such as methyl 4,4-diethoxy-2-butynoate (III) in the presence of potassium hydroxide and 18-crown-6 to provide the appropriately substituted intermediate IV which is a 3:1 mixture of E and Z isomers, the separation of which is not necessary for the final transformation step. The intermediate IV is converted into title products I by hydrolysis with dilute hydrochloric acid in dioxane. The acetylenic esters of type III can be made by processes known to those skilled in the art such as those described by Barbot and Miginiac, Bull. Soc. Chem. France, 1983, 2, p. 41.

The following specific examples are included for illustrative purposes only and are not to be construed as limiting to this disclosure in any way.

EXAMPLE 1

Preparation of 4-([1,1'-Biphenyl]-4-yloxy)-5-hydroxy-2(5H)-furanone

Step 1: Preparation of E,Z-Methyl 4,4-diethoxy-3-(4-phenylphenoxy)-2-butenoate

To a solution of 1.72 g (10 mmol) of 4-phenylphenol in 40 mL of THF was added 0.85 g (15 mmol) of powdered KOH and 3.98 g (15 mmol) of 18-crown-6. The solution was heated to 50° C. for 15 minutes, whereupon 2.8 g (15 mmol) of methyl 4,4-diethoxy-2-butynoate was added. The mixture was stirred for 30 minutes, then allowed to cool to room temperature. The solution was then poured into water, and extracted 3 times with 40 mL of ethyl acetate. The organic layers were combined, dried (MgSO$_4$) and concentrated. The crude oil was subjected to column chromatography on SiO$_2$. Elution with 20% EtOAc-hexane yielded 1.5 g (63%) of a light yellow oil. The E, Z mixture was used in the next step without separation.

NMR (400 MHz, DMSO) Isomer 1: δ 7.59–7.49 (m, 4H, ArH), 7.46–7.28 (m, 3H, ArH), 7.12 (d, J=9 Hz, 2H, ArH), 6.35 (s, 1H, C=CH), 5.04 (s, 1H, OCH), 3.91–3.71 (m, 4H, OCH$_2$), 3.63 (s, 3H, OCH$_3$), 1.32 (t, J=7 Hz, 6H, CH$_3$). Isomer 2: δ 7.59–7.49 (m, 4H, ArH), 7.46–7.28 (m, 3H, ArH), 7.08 (d, J=9 Hz, 2H, ArH), 6.05 (s, 1H, C=CH), 4.95 (s, 1H, OCH), 3.91–3.71 (m, 4H, OCH$_2$), 3.61 (s, 3H, OCH$_3$). 1.39 (t, J=7 Hz, 6H, CH$_3$).

Step 2: Preparation of title compound 1.5 g of E, Z-methyl 4,4-diethoxy-3-(4-phenylphenoxy)-2-butenoate (4.2 mmol) was dissolved in 40 mL of dioxane and 3 mL of 20% (V/V) HCl was added. The solution was heated to reflux for 3 hr then cooled to room temperature. The solvent was removed in vacuo and the HCl removed from the residue by azeotroping 3 times with acetone. The crude yellow solid was triturated with ether to provide 0.76 g (67%) of essentially pure amorphous white solid. Recrystallization from EtOAc: hexane provided 0.66 g of analytically pure product, m.p. 192°–193° C.

NMR (400 MHz, DMSO) δ 8.16 (d, J=9 Hz, 1H OH), 7.77 (d, J=8 Hz, 2H ArH), 7.68 (d, J=7 Hz, 2H, ArH), 7.45 (t, J=8 Hz, 2H, ArH), 7.39(m, 3H, ArH), 6.17 (s, d, J=9 Hz, 1H, COH), 5.14 (s, 1H, C=CH).

IR: 3320 (OH), 1725 (C=O) 1635 (C=C) cm$^{-1}$.

Anal. Calcd. for $C_{16}H_{12}O_4$: C, 71.64; H, 4.51. Found: C, 71.68; H, 4.38.

EXAMPLE 2

5-Hydroxy-4-{4-[4'-(2-hydroxy-5-oxo-2,5-dihydrofuran-3-yloxy)-benzoyl]-phenoxy}-5H-furan-2-one Step 1: Preparation of E, Z-3,3'-[4,4'-carbonyl-bis(-phenoxy)]-bis(4,4-diethoxy-but-2-enoic acid) dimethyl ester To a solution of 2.14 g (10 mmol) of 4,4'-dihydroxy benzophenone in methanol was added 0.15 g (26 mmol) of KOH pellets. After stirring for 1 hr at room temperature the bulk of the methanol was removed in vacuo and the final traces removed from the residue by azeotroping with chloroform and then ether until a light yellow solid was obtained. To this dipotassium salt was added 4.0 g (22 mmol) of methyl 4,4-diethoxy-2-butynoate and 5.8 g (22 mmol) of 18-crown-6. The solution was refluxed for 2 hr, whereupon a slight excess of KOH pellets was added and stirring continued for several hours more. At the end of this time the solution was poured into water and extracted twice with EtOAc. The organic layers were combined, dried (MgSO$_4$) and concentrated and then the residue was subjected to column chromatography on SiO$_2$ to provide 6.5 g of an amber oil.

Step 2: Preparation of title compound.

The product from Step 1 was dissolved in 100 ml of dioxane and 5 ml of 20% HCl was added. The solution was heated to 80° C. for 2 hr, then allowed to cool to room temperature. The solution was concentrated, then azeotroped first with acetone 3 times, then twice with acetone:chloroform. The semisolid residue was then triturated with ether upon which a white powder formed. Filtration provided 2.7 g of the monohydrate of the title compound (63% overall yield from 4,4'-dihydroxy benzophenone), mp 125°–128° C.

NMR (400 MHz, DMSO) δ 8.20 (d, J=9 Hz, 2H, OH), 7.90 (d, J=8 Hz, 4H, ArH), 7.49 (d, J=8 Hz, 4H, ArH), 6.20 (d, J=9 Hz, 2H, CH) 5.31 (S, 2H, C=CH).

IR: 3430 (OH), 1765 (C=O) 1640 (C=C) 1595 (C=C) cm$^{-1}$.

Anal. Calcd. for $C_{21}H_{14}O_9$: C, 61.47; H, 3.44. Found: C, 58.98; H, 3.83.

EXAMPLE 3

Preparation of 4-(4-Octylphenoxy)-5-hydroxy-2(5H)-furanone

Step 1: Preparation of E, Z-methyl 4,4-diethoxy-3-(4-octylphenoxy)-2-butenoate.

To a solution of 2.06 g (10 mmol) of 4-octylphenol in 50 mL of THF was added 0.85 g (15 mmol) of powdered KOH and 3.98 g (15 mmol) of 18-crown-6. The solution was heated to 50° C. for 15 minutes, whereupon 2.8 g (15 mmol) of methyl 4,4-diethoxy-2-butynoate was added. The mixture was stirred for 30 minutes, then allowed to cool to room temperature. The solution was then poured into water, and extracted 3 times with 40 mL of ethyl acetate. The organic layers were combined, dried (MgSO$_4$) and concentrated. The crude oil was subjected to column chromatography on SiO$_2$. Elution with 20% ethyl acetate-hexane yielded 2.1 g (54%) of an oil, used in the next step without further purification.

Step 2: Preparation of title compound 2.1 g of the above ester was dissolved in 60 mL of dioxane and 4 mL of 20% (V/V) HCl was added. The solution was refluxed for 3 hr then cooled to room temperature. The solvent was removed in vacuo and the HCl removed from the residue by azeotroping 3 times with acetone. The crude solid was triturated with ether then recrystallized from ethyl acetate-hexane to provide 1.03 g (63% yield) of product, m.p. 59°–61° C.

NMR (400 MHz, DMSO) d 7.23 (d, J=8 Hz, 2H, ArH), 7.07 (d, J=8 Hz, 2H, ArH), 6.11 (bs, 1H, CHO), 4.97 (s, 1H, C=CH), 4.10 (bs, 1H, OH), 2.61 (t, J=8 Hz, 2H, CH$_2$Ar), 1.62 (m, 2H), 1.31 (m, 10H), 0.88, (t, J=7 Hz, 3H, CH$_3$).

Anal. Calcd. for $C_{18}H_{24}O_4$: C, 69.22; H, 6.20. Found: C, 69.00; H, 6.12.

EXAMPLE 4

Preparation of 4-(4-Cyclopentylphenoxy)-5-hydroxy-2(5H)-furanone.

Step 1: Preparation of E, Z-methyl 4,4-diethoxy-3-(4-cyclopentylphenoxy)-2-butenoate To a solution of 2.42 g (15 mmol) of 4-cyclopentylphenol in 50 mL of THF was added 1.12 g (20 mmol) of powdered KOH and 5.28 g (20 mmol) of 18-crown-6. The solution was heated to 50° C. for 15 minutes, whereupon 3.73 g (20 mmol) of methyl 4,4-diethoxy-2-butynoate was added. The mixture was stirred for 30 minutes, then allowed to cool to room temperature. The solution was then poured into water, and extracted 3 times with 40 mL of ethyl acetate. The organic layers were combined, dried (MgSO$_4$) and concentrated. The crude oil was subjected to column chromatography on SiO$_2$. Elution with 20% ethyl acetate-hexane yielded 2.01 g (58%) of an oil, used in the next step without further purification.

Step 2: Preparation of title compound 2.0 g (5.7 mmol) of the above ester was dissolved in 60 mL of dioxane and 4 mL of 20% (V/V) HCl was added. The solution was refluxed for 3 hr then cooled to room temperature. The solvent was removed in vacuo and the HCl removed from the residue by azeotroping 3 times with acetone. The crude solid was triturated with ether then recrystallized from ethyl acetate-hexane to provide 0.97 g of product. 66% yield, m.p. 101°–103° C.

NMR (400 MHz, DMSO) d 8.12 (d, J=9 Hz, 1H, OH), 7.34 (d, J=8 Hz, 2H, ArH), 7.18 (d, J=8 Hz, 2H, ArH), 6.12 (d, J=9 Hz, 1H, COH), 5.00 (s, 1H, C=CH), 2.97 (m, 1H, CHAr), 2.02 (m, 2H), 1.75 (m, 2H), 1.64 (m, 2H), 1.47 (m, 2H).

Anal. Calcd. for $C_{15}H_{16}O_4$: C, 62.22; H, 6.20. Found: C, 62.93; H, 5.88.

EXAMPLE 5

Preparation of 4-(4-Trifluoromethylphenoxy)-5-hydroxy-2(5H)-furanone

Step 1: Preparation of E, Z-methyl 4,4-diethoxy-3-(4-trifluoromethylphenoxy)-2-butenoate To a solution of 2.43 g (15 mmol) of 4-trifluoromethylphenol in 40 mL of THF was added 1.12 g (20 mmol) of powdered KOH and 5.28 g (20 mmol) of 18-crown-6. The solution was heated to 50° C. for 15 minutes, whereupon 3.73 g (20 mmol) of methyl 4,4-diethoxy-2-butynoate was added. The mixture was stirred for 30 minutes, then allowed to cool to room temperature. The solution was then poured into water, and extracted 3 times with 40 mL of ethyl acetate. The organic layers were combined, dried (MgSO$_4$) and concentrated. The crude oil was subjected to column chromatography on SiO$_2$. Elution with 20% ethyl acetate-hexane yielded 2.31 g (65%) of an oil, used in the next step without further purification.

Step 2: Preparation of title compound 2.3 g (6.6 mmol) of the above ester was dissolved in 60 mL of dioxane and 4 mL of 20% (V/V) HCl was added. The solution was refluxed for 3 hr then cooled to room temperature. The solvent was removed in vacuo and the HCl removed from the residue by azeotroping 3 times with acetone. The crude solid was triturated with ether then recrystallized from ethyl acetate-hexane to provide 0.92 g (54%) of product, m.p. 87°–89° C.

NMR (400 MHz, CDCl$_3$) δ 7.72 (d, 8 Hz, 2H, ArH), 7.35 (d, J=8 Hz, 2H, ArH), 6.17 (d, J=9 Hz, 1H, CH), 5.04 (S, 1H, =CH), 5.01 (d, J=9 Hz, 1H, OH).

IR: 3280, 1755, 1730, 1650, 1320 cm$^{-1}$.

Anal. Calcd. for $C_{11}H_{17}O_4$: C, 50.78; H, 2.71. Found: C, 50.40; H, 2.87.

EXAMPLE 6

Preparation of 4,4'-[Biphenyl-4,4'-diyl-bis (oxy)]-bis-(5-hydroxy-2(5H)-furanone)

Step 1: Preparation of E, Z-3,3'-[4,4'-biphenyl]-bis(4,4-diethoxy-but-2-enoic acid) dimethyl ester To a solution of 1.86 g (10 mmol) of 4,4'-biphenol in methanol was added 1.5 g (26 mmol) of KOH pellets. After stirring for 1 hr at room temperature the bulk of the methanol was removed in vacuo and the final traces removed from the residue by azeotroping with chloroform then ether until a light yellow solid was obtained.

To this di-potassium salt was added 4.0 g (22 mmol) of methyl 4,4-diethoxy-2-butynoate and 5.8 g (22 mmol) of 18-crown-6. The solution was refluxed for 2 hr, whereupon a slight excess of KOH pellets was added and stirring continued for several hours more. At the end of this time the solution was poured into water and extracted twice with EtOAc. The organic layers were combined and dried (MgSO$_4$) then the residue was subjected to column chromatography on SiO$_2$ to provide 3.4 g of the diester as an amber oil.

Step 2. Preparation of title compound

The product from Step 1 was dissolved in 100 ml of dioxane and 5 ml of 20% HCl was added. The solution was heated to 80° C. for 2 hr, then allowed to cool to room temperature. The solution was concentrated, then azeotroped first with acetone 3 times, then twice with acetone: chloroform. The semisolid residue was then triturated with ether from which a white powder formed. Filtration provided 0.88 g (38%) of product, m.p. 258°-260° C.

NMR (400 MHz, DMSO) δ 8.16 (d,J=9 Hz, 2H, OH), 7.82 (d, J=9 Hz, 4H ArH), 7.40 (d, J=9 Hz,4H, ArH), 6.17 (d, J=9 Hz, 2H, CH), 5.15 (s, 2H C=CH).

IR: 3280, 1755, 1730, 1650, 1320 cm$^{-1}$.

Anal. Calcd. for C$_{11}$H$_{17}$O$_4$: C, 62.83; H, 3.69. Found: C, 62.51; H, 3.90.

EXAMPLE 7

Preparation of
4-[4-thiophenyl-1-phenoxy]-5-hydroxy-2(5H)-furanone

Step 1: Preparation of E, Z-methyl 4,4-diethoxy-3-(4-thiophenyl-1-phenoxy)-2-butenoate To a solution of 2.02 g (10 mmol) of 4-thiophenylphenol in 40 mL of THF was added 0.85 g (15 mmol) of powdered KOH and 3.98 g (15 mmol) of 18-crown-6. The solution was heated to 50° C. for 15 minutes, whereupon 2.79 g (15 mmol) of methyl 4,4-diethoxy-2-butynoate was added. The mixture was stirred for 30 minutes, then allowed to cool to room temperature. The solution was then poured into water, and extracted 3 times with 40 mL of ethyl acetate. The organic layers were combined, dried (MgSO$_4$) and concentrated. The crude oil was subjected to column chromatography on SiO$_2$. Elution with 20% ethyl acetate-hexane yielded 2.13 g (55%) of an oil, used in the next step without further purification.

Step 2: Preparation of title compound 2.13 g (5.5 mmol) of the above ester was dissolved in 60 mL of dioxane and 4 mL of 20% (V/V) HCl was added. The solution was refluxed for 3 hr then cooled to room temperature. The solvent was removed in vacuo and the HCl removed from the residue by azeotroping 3 times with acetone. The crude solid was triturated with ether then crystallized from ethyl acetate: hexane to yield 1.3 g 84% of white powder, m.p. 131°-132° C.

NMR (400 MHz, DMSO) δ 8.14 (d, J=9 Hz, 1H, OH), 7.42-7.26 (m, 9H, ArH), 6.13 (d, J=9 Hz, 1H, CHO), 5.15 (s, 1H, C=CH).

IR: 3250, 1720, 1650 cm$^{-1}$.

Anal. Calcd. for C$_{16}$H$_{12}$O$_4$S: C, 63.99; H, 4.03. Found: C, 63.33; H, 3.88.

EXAMPLE 8

Preparation of
5-Hydroxy-4-(4-phenoxyphenoxy)-2(5H)-furanone

Step 1: Preparation of E, Z-methyl 4,4-diethoxy-3-(4-phenoxyphenoxy)-2-butenoate To a solution of 2.79 g (15 mmol) of 4-phenoxyphenol in 40 mL of THF was added 1.14 g (20 mmol) of powdered KOH and 5.28 g (20 mmol) of 18-crown-6. The solution was heated to 50° C. for 15 minutes, whereupon 3.72 g (20 mmol) of methyl 4,4-diethoxy-2-butynoate was added. The mixture was stirred for 30 minutes, then allowed to cool to room temperature. The solution was then poured into water, and extracted 3 times with 40 mL of ethyl acetate. The organic layers were combined, dried (MgSO$_4$) and concentrated. The crude oil was subjected to column chromatography on SiO$_2$. Elution with 20% ethyl acetate-hexane yielded 3.02 g (55%) of an oil, used in the next step without further purification.

Step 2: Preparation of title compound 3.02 g (8.1 mmol) of the above ester was dissolved in 60 mL of dioxane and 4 mL of 20% (V/V) HCl was added. The solution was refluxed for 3 hr then cooled to room temperature. The solvent was removed in vacuo and the HCl removed from the residue by azeotroping 3 times with acetone. The crude solid was triturated with ether then crystallized from ethyl acetate: hexane to yield 1.55 g (63%) of product, m.p. 107°-108° C.

NMR (400 MHz, DMSO) δ 8.12 (d, J=8 Hz, 1H OH), 7.39 (m, 2H, ArH), 7.29 (d, J=9 Hz, 2H ArH), 7.15 (m, 1H, ArH), 7.09 (d, J=9 Hz, 2H ArH), 6.13 (d, J=8 Hz, 1H, COH), 5.10 (s, 1H C=CH).

Anal. Calcd. for C$_{16}$-H$_{12}$O$_4$S: C, 67.60; H, 4.25. Found: C, 67.27; H, 3.86.

PHARMACOLOGY AND PHARMACEUTICAL COMPOSITION

Immobilization Dependent Bone Loss in the Rat Femur

This assay was performed according to the procedure described by Kharode Y.P., Kowal D., O'Rourke S., and Hayward M., "Effect of Time and Pharmacologic Intervention on Bone Mineralization," J. Bone Min. Res. 2, Supp.1. (1987).

Bone mass was determined in the contralateral femora from ovariectomized rats which had been subjected to unilateral sciatic nerve severance. After sciatic neurotomy, the rats were treated with test compound for 2 to 4 weeks. The rats were euthanized, the femora were excised, debrided of soft tissue, and then dehydrated. After drying, the mass of each pair of femora was determined by weighing. The % change in bone mass is calculated using the formula:

$$\frac{(\text{wt. of intact limb}) - (\text{wt. of severed nerve limb})}{(\text{wt. of intact limb})}$$

The bone mass data is summarized in Table 1, which demonstrates the significant retention of bone in immobilized femora in rats treated with title compounds relative to femora from vehicle treated control rats.

TABLE I

| Effect of Invention Compound on Bone Mass Change | | | |
|---|---|---|---|
| Treatment Compound | Dosage (mg/kg, i.p.) | Regimen | % Change in Bone Mass |
| Ex. 2 | 50 | 5×/week for 2 weeks | 9.0* ± 1.1 |
| Ex. 6 | 50 | 5×/week for 2 weeks | 7.6* ± 0.7 |
| Ex. 1 | 20 | 5×/week for 4 weeks | 4.8 ± 0.6 |

*p <0.05 vs. vehicle $^{45}$Ca Release from Rat Limb Bone

Step (1): Limb Bone Preparation

Timed pregnant Sprague-Dawley CD rats (Charles River) are administered 100 uCi $^{45}$CaCl$_2$ (NEN calcium-45 NEZ-013) in 100 μl of 0.9% saline, subcutaneously, on day 18 of gestation. The rats are sacrificed the following day by asphyxiation. The fetuses are removed and the right forelimbs excised and placed in a Petri dish containing ice cold explant medium consisting of modified BGJb-Fitton Jackson media (custom formulation, Gibco No. 78-0088) adjusted to pH 7.3 to which 10 mM TES [N-tris-(hydroxymethyl)methyl-2-aminoethanesulfonic acid] is added. The modified BGJb media is obtained without salts glucose or bicarbonate and is supplemented before use with 0.1 mM MgCl$_2$, 1.25 mM CaCl$_2$, 5.3 mM KCl, 0.7 mM MgSO$_4$, 130 mM NaCl, 1.0 mM NaH$_2$PO$_4$, 1 g/1 glucose, 50 mg/1 Na acetate and 100 U/ml penicillin G. The medium is sterilized by passage through a 0.2 μM filter (Nalge). Under a dissecting microscope, the bones are gently cleaned of adherent tissue and the cartilagenous ends removed.

Step (2): Incubation and Drug Treatment

The midshafts are placed, individually, on 3×3 mm squares of filter paper (Gelman GN-6 metricel filters; 0.45 μM pore size) which rest on stainless steel screens in wells of 24-well culture plates containing 0.5 ml of preincubation medium. The preincubation medium is brought to 37 deg. C. prior to transfer of bones. The preincubation medium consists of the modified BGJb medium (with salts and glucose as above), pH 7.3, containing 29 mM NaHCO$_3$. After incubation for 18-24 hours at 37° C. in 5% CO$_2$, the bones are transferred on their screen/filter paper supports to new plates containing, in a total volume of 0.5 ml/well at 37° C., the test compound diluted in preincubation medium supplemented with 15% heat inactivated horse serum (Gibco No. 230-6050), pH 7.3, with or without a bone resorption stimulating agent (parathyroid hormone [PTH]). For compounds that require nonaqueous solvents, dilutions are made from the appropriate stock solution with medium. In these instances, basal and bone resorption stimulated controls exposed to an equivalent concentration of the vehicle are included. An additional group of bones that have been subjected to boiling for 1 hour are used to establish background, non cell mediated, exchange of $^{45}$Ca. The right ulna and radius from each fetus are used. Both bones are subjected to the same treatment and each treatment group consists of bones from 4 or more fetuses. Treatments are randomly assigned using a preclinical statistics program (PS-ALLOC). After a 48 hour incubation at 37° C. in 5% CO$_2$, the bones are removed from the medium and extracted in 0.5 ml of 0.1N HCl for 1 or more days. Duplicate 150 μl aliquots of the incubation medium and the bone extract are analyzed for $^{45}$Ca radioactivity in 5 ml of liquid scintillation cocktail.

The percentage of bone $^{45}$Ca released into the medium is determined as follows:

$$\frac{^{45}\text{Ca CPM in medium}}{^{45}\text{Ca CPM in medium} + {}^{45}\text{Ca CPM in bone}}$$

Results are normally expressed as the ratio of the percent $^{45}$Ca release of the experimental group verses the appropriate vehicle control. Normalization of the basal bone resorption to 1.00 leads to ratios for bone resorption agents such as PTH ($10^{-7}$M) that are significantly greater than 1.00 (commonly 1.3-2.0) and to a background ratio for the controls that is significantly less than 1.00 (commonly 0.5-0.7). A regression analysis is calculated for dose response and the concentration of test compound required to inhibit bone resorption ($^{45}$Ca release) is reported (Table II).

TABLE II

| Inhibition of Bone Resorption ($^{45}$Ca release) | |
|---|---|
| Compound | MIC (μg/mL) |
| 1 | 10 |
| 3 | 10 |
| 4 | 1 |
| 5 | IC$_{50}$ = 3.5 |
| 7 | 10 |
| 8 | 10 |

The compounds of formula (I) of this invention are used alone or in combination with pharmacologically acceptable carriers, the proportion of which is determined by the solubility and chemical nature of the compound, chosen route of administration and standard medical practice. For example, they are administered orally in the form of capsules, tablets, suspensions or solutions or they may be injected parenterally. Capsules or tablets are the preferred mode of administration. For parenteral administration they can be used in the form of a sterile solution containing other solutes, for examples enough saline or glucose to make the solution isotonic.

The capsule and tablet compositions contain the active ingredient in admixture with nontoxic pharmaceutical excipients known to be suitable in the manufacture of capsules and tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula (I) contain the active ingredient in admixture with one or more non-toxic pharmaceutical excipients known to be suitable in the manufacture of aqueous suspensions. Suitable excipients are, for example, methylcellulose, sodium aliginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula (I) will vary with the form of administration and the particular compound chosen. Furthermore, it will vary with the particular host as well as the age, weight and condition of the host under treatment, as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects.

What is claimed is:

1. A compound according to the formula:

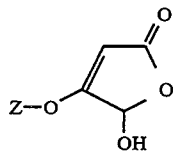

where Z is a group selected from:

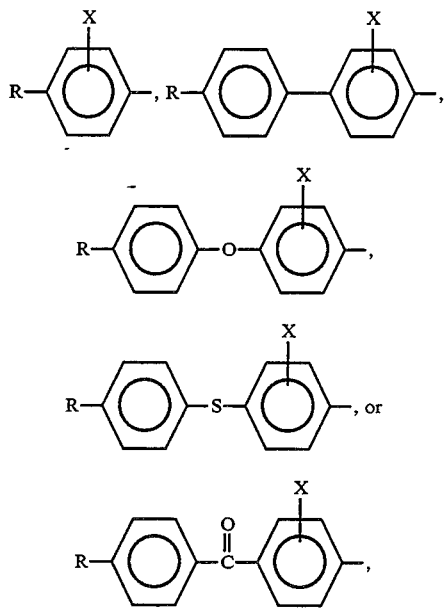

where R is H, halogen, $C_1-C_8$ alkyl, $C_3-C_5$ cycloalkyl, trifluoromethyl, or

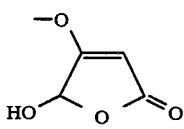

and X is H, $C_1-C_8$ alkyl, —O—$C_1-C_8$ alkyl or halogen.

2. A compound according to claim 1 which is 4-[(1,1'-biphenyl)-4-yloxy]-5-hydroxy-2(5H)-furanone.

3. A compound according to claim 1 which is 4-(4'-cyclopentylphenoxy)-5-hydroxy-2(5H)-furanone.

4. A compound according to claim 1 which is 5-hydroxy-4-55 4-[4'-(2-hydroxy-5-oxo-2,5-dihydrofuran-3-yloxy)benzoyl]phenyoxy}-2(5H)-furanone.

5. A compound according to claim 1 which is 4,4'-[biphenyl-4,4'-diyl-bis(oxy)]-bis-(5-hydroxy-2(5H)-furanone.

6. A compound according to claim 1 which is 4-(4-octylphenoxy)-5-hydroxy-2(5H)furanone.

7. A compound according to claim 1 which is 4-(4-trifluoromethylphenoxy)-5-hydroxy-2(5H)furanone.

8. A compound according to claim 1 which is 4-(4-thiophenyl-1-phenoxy)-5-hydroxy-2(5H)furanone.

9. A compound according to claim 1 which is 5-hydroxy-4-(4-phenoxyphenoxy)-2(5H)furanone.

10. A method of treating osteoporosis in a mammal in need thereof which comprised administration thereto of a therapeutically effective amount of a compound of the formula

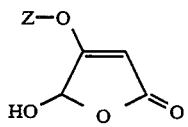

where Z is selected from:

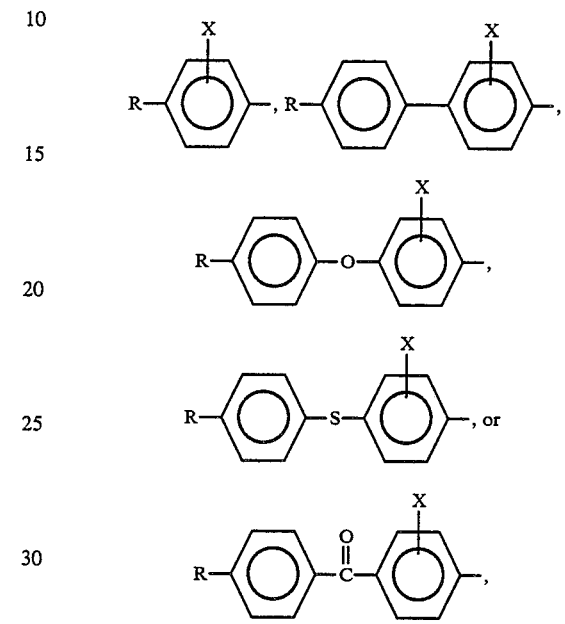

where R is H, halogen, $C_1-C_8$ alkyl, $C_3-C_5$ cycloalkyl, trifluoromethyl, or

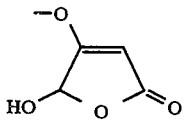

and X is H, $C_1-C_8$ alkyl, —O—$C_1-C_8$ alkyl or halogen.

11. A pharmaceutical composition useful in the treatment of osteoporosis which comprises a pharmaceutically acceptable carrier and a therapeutically effective amount of a compound according to the formula:

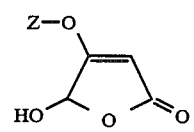

where Z is selected from:

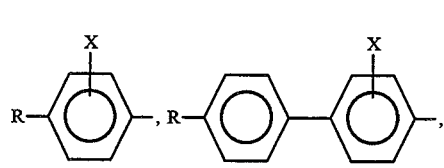

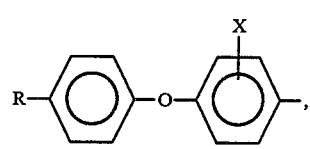

-continued
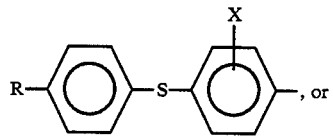, or
-continued
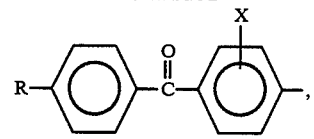,
where R is H, $C_1$–$C_8$ alkyl, $C_3$–$C_8$ cycloalkyl, halogen, trifluoromethyl, or
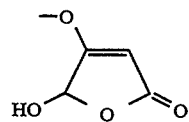
and X is H, $C_1$–$C_8$ alkyl, —O—$C_1$–$C_8$ alkyl or halogen.
* * * * *